United States Patent [19]

DeIulio

[11] Patent Number: 5,383,451
[45] Date of Patent: Jan. 24, 1995

[54] ENDOTRACHEAL TUBE STABILIZATION DEVICE

[76] Inventor: David M. DeIulio, 9744 SW. 125 Terrace, Miami, Fla. 33176

[21] Appl. No.: 713,121

[22] Filed: Jun. 10, 1991

[51] Int. Cl.6 .............................................. A61M 16/00
[52] U.S. Cl. ........................ 128/207.17; 128/DIG. 26
[58] Field of Search ................... 128/200.26, 207.14, 128/207.15, 207.17, DIG. 26

[56] References Cited

U.S. PATENT DOCUMENTS

| | | | |
|---|---|---|---|
| 2,590,006 | 3/1952 | Gordon | 128/DIG. 26 |
| 3,677,250 | 7/1972 | Thomas | 128/DIG. 26 |
| 3,713,448 | 1/1973 | Arrott | 128/DIG. 26 |
| 3,946,742 | 3/1976 | Eross | 128/DIG. 26 |
| 4,331,143 | 5/1982 | Foster | 128/207.14 |
| 4,437,463 | 3/1984 | Ackerman | 128/207.17 |
| 4,465,067 | 8/1984 | Koch et al. | 128/207.18 |
| 4,572,177 | 2/1986 | Tiep et al. | 128/205.17 |
| 4,658,814 | 4/1987 | Anderson | 128/207.17 |
| 4,683,882 | 8/1987 | Laird | 128/207.17 |
| 4,699,139 | 10/1987 | Marshall et al. | 128/207.18 |
| 4,700,432 | 10/1987 | Fennel | 128/DIG. 26 |
| 4,774,943 | 10/1988 | Yu | 128/207.14 |
| 4,867,154 | 9/1989 | Potter et al. | 128/207.17 |

*Primary Examiner*—Edgar S. Burr
*Assistant Examiner*—Aaron J. Lewis
*Attorney, Agent, or Firm*—Rogers, Howell & Haferkamp

[57] ABSTRACT

An endotracheal tube stabilization device includes a length of K-wire having a flattened loop or the like formed on each end thereof for insertion through a slot in a patch of moleskin to thereby secure patches of moleskin at each end thereof. The patches of moleskin may then be applied near the ears of a patient to orient the K-wire about the patient's face and spaced apart therefrom to secure an endotracheal tube thereto and hold it in place.

7 Claims, 1 Drawing Sheet

U.S. Patent     Jan. 24, 1995     5,383,451
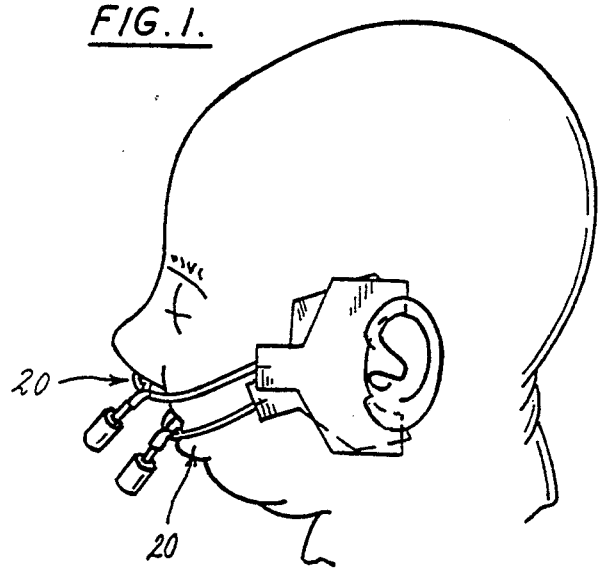
FIG. 1.
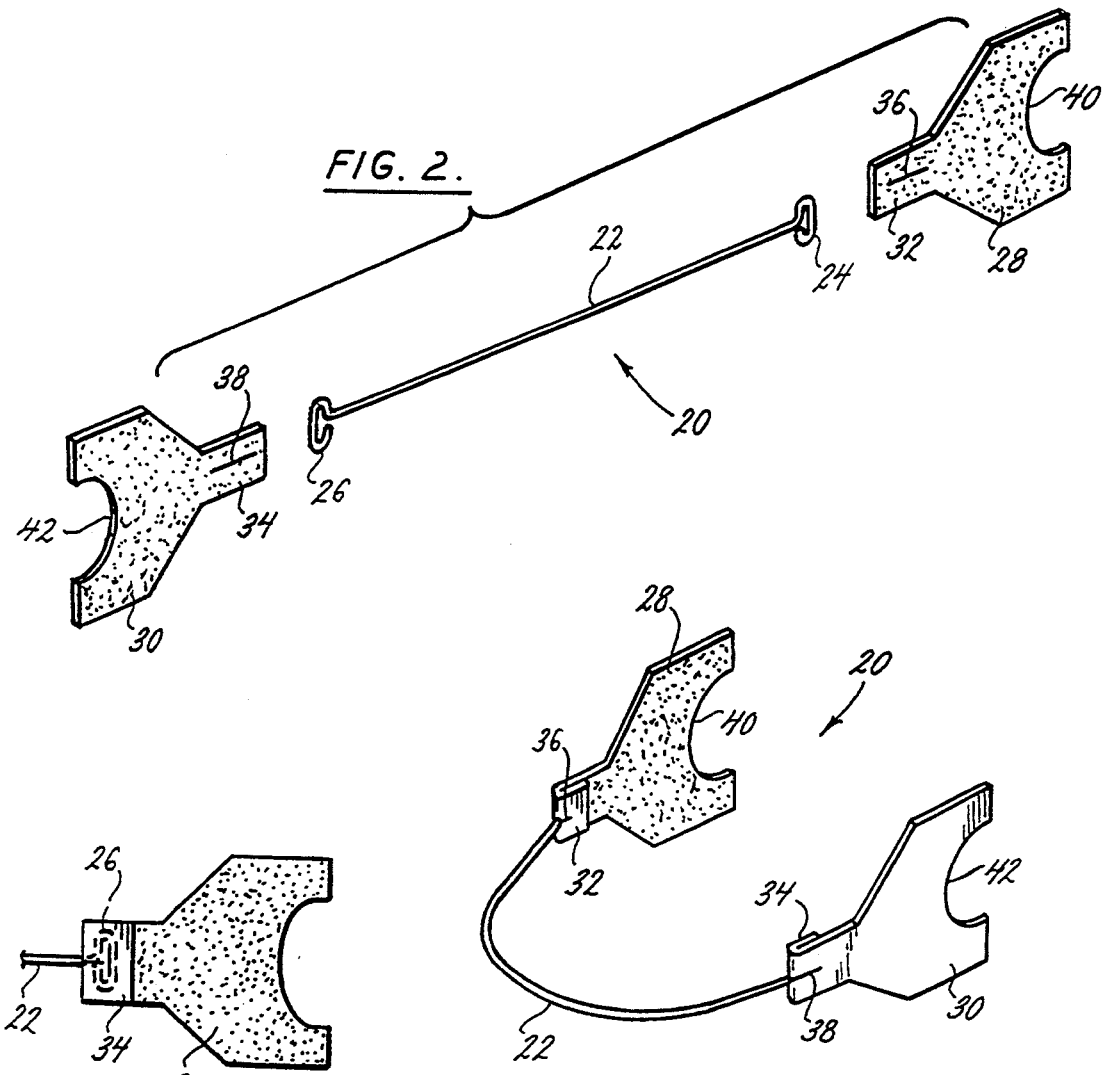
FIG. 2.
FIG. 4.
FIG. 3.

ENDOTRACHEAL TUBE STABILIZATION DEVICE

BACKGROUND AND SUMMARY OF THE INVENTION

Devices are available in the prior art for stabilizing endotracheal tubes or the like which are inserted in the nose or mouth of a patient. In particular, these devices have been developed for use with babies which can exhibit a significant amount of head movement which might otherwise dislodge or extubate the tube. There are many such examples of these devices found in the prior art.

Of those known to the inventor, U.S. Pat. No. 4,867,154 discloses various embodiments of an endotracheal tube stabilizing device which is perhaps most closely related to that of the present invention. In the '154 patent, a framework is supported by a three-point mounting, the forehead and the two zygoma regions (cheekbones) of a framework generally extending over the face of the patient. Various shapes for the framework are suggested, with the framework being attached by Velcro TM pads and taped to the patient's face. As can be appreciated, the framework is suggested as being quite substantial and a tube holder or adapter is secured to the framework through which the endotracheal tube is inserted.

As suggested by most of the prior art, the '154 patent continues the general approach in the prior art of providing a substantial framework which was thought to be necessary in order to secure the endotracheal tube to prevent its being accidentally extubated by the thrashing about of a patient. Unfortunately, these frameworks are undesirable in that if applied to a premature baby or younger infant, they can block the view of the baby's face and cause undue alarm to the baby's parents. Furthermore, these frameworks obscure the baby's face and restrict access to the baby's face for any medical procedures such as suctioning or the like. Furthermore, the frameworks are generally custom-made which increases their expense and also requires that they be sized appropriately for different patients.

In order to solve these and other problems in the prior art, the inventor herein has succeeded in designing and developing an elegantly simple arrangement for stabilizing an endotracheal tube which offers minimal interference with access to the patient's face, and which is also minimally obtrusive to the patient's face (and therefore aesthetically more pleasing). Essentially, the arrangement of the invention includes utilizing a single strand of K-wire which has its ends secured to adhesive patches, such as moleskin, the patches being applied near the baby's ears. The K-wire is sized to extend immediately below the baby's nose or at the level of the mouth, as required, and is simply secured to the endotracheal (or other) tube with a suture or with a small strip of adhesive tape. As compared with the endotracheal stabilizing devices of the prior art, the present invention presents a significant improvement in several different areas. First of all, K-wire can be cut to an appropriate length from available stocks of K-wire, and moleskin patches may be used from available stocks of moleskin such that no special apparatus, patches of Velcro TM, frameworks, or the like are required in order to form the present inventive arrangement. Consequently, the present invention represents a significantly smaller cost and completely eliminates any requirement of inventory of different sized devices. While providing minimal interference with access to the baby's face, the device has been found to be more than capable of holding the endotracheal tube in place as the baby thrashes about. Additionally, by eliminating the significant structure found in other prior art devices, the present invention actually minimizes the potential for injury to an infant.

The moleskin patches attaching the ends of the K-wire may be properly oriented upon application to put the K-wire adjacent a tube inserted in the nose or the mouth, as desired. Thus, the same device may be utilized for either while in the prior art different devices were typically used. This feature exhibits the versatility of the present invention. Furthermore, as the moleskin patches are placed proximal to and anterior to the ears, a wider base of support is provided than those prior art devices which secured a supporting framework on the face of the patient, such as in the '154 patent. This placement also prevents loosening of the moleskin due to a baby's salivation, which is the major problem currently encountered in the commonly used practice of taping the tube to the perioral area.

While standard K-wire may be utilized and is shown in the preferred embodiment, non-metallic or non-magnetic "wires" may be utilized instead such that the device will not interfere with MRI imaging scanners or the like. The "wire" need only be sufficiently malleable and long enough to be properly oriented over the patient's face.

Still another feature of the device is the ability to effectively "mark" the position on the tube whereat the K-wire is positioned so that replacement tubes, or the replacement of tubes which have been extubated for any reason, may be positioned at exactly the same place. This thereby decreases the need for subsequent radiographs to verify placement of the tube. In addition, reintubation does not require removal of the device, unlike any existing stabilizer.

While the principal advantages and features of the invention have been explained above, a more thorough understanding may be attained by referring to the drawings and description of the preferred embodiment which follow.

BRIEF DESCRIPTION OF THE DRAWINGS

FIG. 1 is a perspective view of a patient with the apparatus of the present invention applied to retain tubes in both the nose and mouth;

FIG. 2 is a perspective view of the various parts used to comprise the invention;

FIG. 3 is a perspective view of the invention fully assembled; and

FIG. 4 is a side view of one of the adhesive patches detailing its mounting to a wire end.

DETAILED DESCRIPTION OF THE PREFERRED EMBODIMENT

The endotracheal tube stabilization device 20 of the present invention is shown in FIGS. 2-4 and includes a K-wire 22 having a loop 24, 26 formed on either end thereof. A pair of adhesive patches 28, 30 each have a tab 32, 34 through which a slot 36, 38 has been cut to accept the loops 24, 26 of K-wire 22 for attachment purposes. This is best shown in FIGS. 3 and 4 wherein a portion of the tabs 32, 34 are folded over the loops 24, 26. Thus, the K-wire 22 is secured at its ends to each of adhesive patches 28, 30.

The adhesive patches 28, 30 may be formed from mole skin, or some other appropriate adhesive product which may readily attach to the skin of a patient and yet be removed therefrom without injury to the patient. Each adhesive patch 28, 30 has an arcuate cutout 40, 42 to facilitate its close placement adjacent the ear of a patient, such as a small baby. This is best shown in FIG. 1.

In operation, the stabilization apparatus 20 is first assembled into the arrangement shown in FIG. 3 wherein the K-wire 22 has been bent into an orientation which closely approximates its final position. The mole skin is then applied adjacent the ears of the patient, as shown in FIG. 1. The K-wire is bent and formed to conform with and lie close to the surface of the patient's face to enhance the stability of the device. Thereafter, the endotracheal tube is inserted, and the K-wire 22 is secured to a desired location on the tube by a suture, small strip of adhesive tape, or the like, all as is well known in the art. In this manner, and as is shown in FIG. 1, a minimal obstruction is presented above the patient's face and, yet, the endotracheal tube is securely held in place.

While typical, on-hand, materials have been disclosed in the preferred embodiment, it is well understood to one of ordinary skill in the art that other materials may be readily substituted therefor. For example, a non-metallic or non-magnetic material, such as plastic or the like, may be substituted for the K-wire to facilitate MRI scanning of the patient without removal of the stabilization apparatus. Additionally, other methods may be used to attach the ends of the K-wire to the adhesive patches, and other means may be used other than adhesive patches to secure the ends of the K-wire to the patient's head. In addition, the size and shape of the adhesive patches may be modified. All of these alternative materials and methods are within the scope and teaching of the present invention.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. An apparatus for stabilizing an endotracheal tube inserted in either the nose or mouth of a patient, said stabilization apparatus comprising a wire having opposing first and second terminal ends, means for securing said first and second terminal ends of said wire substantially adjacent the ears of the patient so that said wire spans the patient's face proximate the nose or mouth and is held in place a spaced distance thereabove, and means for securing said wire to said endotracheal tube.

2. The apparatus of claim 1 wherein the wire ends securing means comprises a patch of adhesive applied to the patient's face near each ear, said first and second terminal ends of said wire being secured to said patches.

3. The apparatus of claim 2 wherein said wire is standard K-wire.

4. The apparatus of claim 2 wherein said wire is non-metallic to thereby be non-interfering for MRI scanners.

5. The apparatus of claim 2 wherein said patches are made of moleskin, and wherein each patch has a tab with a slot formed therein, each wire end having a loop formed therein for insertion through said slot, each tab being sufficiently long so that a portion thereof may be folded over said slot to thereby secure the wire end.

6. An apparatus for stabilizing an endotracheal tube inserted in either the nose or mouth of a patient, said stabilization apparatus comprising a K-wire having opposing first and second terminal ends, and a patch of moleskin secured to each end of said K-wire, said K-wire having a sufficient length so that as said moleskin patches are secured proximate the patient's ears, said K-wire extends across the patient's face proximate the nose or mouth, as desired, and a spaced distance thereabove as convenient for securing said endotracheal tube thereto.

7. The apparatus of claim 6 wherein each patch of moleskin has a slot with an overlapping portion, and each K-wire end is formed in a loop for insertion into said slot, said overlapping portion thereafter overlapping said loop to secure said K-wire to said moleskin patch.

* * * * *